United States Patent
Yoo et al.

(10) Patent No.: US 11,593,939 B2
(45) Date of Patent: Feb. 28, 2023

(54) MULTIPLE SKIN LESION DETECTION SYSTEM, MULTIPLE SKIN LESION DETECTION METHOD AND COMPUTER-READABLE RECORDING MEDIUM HAVING PROGRAM FOR IMPLEMENTING SAME RECORDED THEREON

(71) Applicant: LULULAB INC., Seoul (KR)

(72) Inventors: Sangwook Yoo, Seoul (KR); YongJoon Choe, Seoul (KR); Seo Young Oh, Seoul (KR); Shohrukh Bekmirzaev, Seoul (KR)

(73) Assignee: LULULAB INC., Seoul (KR)

( * ) Notice: Subject to any disclaimer, the term of this patent is extended or adjusted under 35 U.S.C. 154(b) by 0 days.

(21) Appl. No.: 17/733,174

(22) Filed: Apr. 29, 2022

(65) Prior Publication Data
US 2022/0261993 A1 Aug. 18, 2022

Related U.S. Application Data (63) Continuation of application No. PCT/KR2020/006534, filed on May 19, 2020.

(51) Int. Cl.
*G06T 7/00* (2017.01)
*G06V 40/16* (2022.01)
*G06V 10/764* (2022.01)
*A61B 5/00* (2006.01)

(52) U.S. Cl.
CPC ............ *G06T 7/0012* (2013.01); *A61B 5/444* (2013.01); *G06V 10/764* (2022.01); *G06V 40/168* (2022.01); *G06T 2207/20084* (2013.01); *G06T 2207/30088* (2013.01); *G06T 2207/30096* (2013.01); *G06T 2207/30201* (2013.01)

(58) Field of Classification Search
None
See application file for complete search history.

(56) References Cited

FOREIGN PATENT DOCUMENTS

| CN | 110555830 A | 12/2019 |
|---|---|---|
| KR | 10-1969346 B1 | 4/2019 |
| KR | 10-2019-0051256 A | 5/2019 |
| KR | 10-2020-0083100 A | 7/2020 |

OTHER PUBLICATIONS

Nils Gessert et al., "Skin Lesion Classification Using CNNs With Patch-Based Attention and Diagnosis-Guided Loss Weighting", IEEE Transactions on Biomedical Engineering, vol. 67, Issue 2, May 9, 2019.

Lei Zhang et al., "Automatic skin lesion segmentation by coupling deep fully convolutional networks and shallow network with textons", Journal Medical Imagaging 6(2), 024001 Apr.-Jun. 2019, 13 pages.

*Primary Examiner* — Samah A Beg
(74) *Attorney, Agent, or Firm* — Sughrue Mion, PLLC (57) ABSTRACT

The present invention relates to a deep learning-based multiple skin lesion detection system, a multiple lesion detection method, and a computer-readable recording medium that has a program for implementing same recorded thereon. The system according to the present invention enables accurate classification and detection of various skin lesions having similar characteristics, on the basis of a context-dependent decision-making structure in which the local spatial correlation between various skin lesions in skin is considered.

14 Claims, 6 Drawing Sheets

MULTIPLE SKIN LESION DETECTION SYSTEM, MULTIPLE SKIN LESION DETECTION METHOD AND COMPUTER-READABLE RECORDING MEDIUM HAVING PROGRAM FOR IMPLEMENTING SAME RECORDED THEREON

CROSS REFERENCE TO RELATED APPLICATIONS

This application is a continuation of Application No. PCT/KR2020/006534 filed on May 19, 2020, the entire contents of which is hereby incorporated by reference.

TECHNICAL FIELD

The present invention relates to a multiple skin lesion detection system, a multiple skin lesion detection method, and a computer-readable medium in which a program for implementing the same is recorded.

The present invention also relates to a multiple skin lesion detection method and a multiple skin lesion detection system, wherein a situation-dependent decision determination process in which a local spatial correlation between different skin lesions is considered, and a computer-readable medium in which a program for implementing the same is recorded.

BACKGROUND ART

Current products for facial skin analysis utilize simple image processing technology or only detect a small number of skin lesions even if artificial intelligence models are used, so there is a limitation in detecting various skin problems depending on the surrounding environments and users.

Further, since skin problems involve similar characteristics, it is important to consider a correlation between objects to be detected so as to accurately detect the same.

However, the objects to be detected have been independently considered in related studies to date. Object detection tasks in major machine learning vision challenges such as COCO, Pascal VOC 2012, Cityscaps, CamVid, etc., are based on "context-independent decision" wherein a decision to an object in the detection is independent of results in relation to other objects.

When the situation-independent decision method-based artificial intelligence technology is applied to detection of skin problems, characteristics of skin objects similar to one another become an impediment to learning each class of the objects and, eventually, there is a demerit of inaccurately judging or misjudging the skin object problems. For example, it may be difficult to accurately distinguish between freckles, post-inflammatory pigmentation and acne depending on lighting environments for photographing.

[Prior Art Disclosure]
[Patent Document 1] Korean Laid-Open Patent Publication No. 2018-0041919

DISCLOSURE

Technical Problem

The present invention provides a multiple skin lesion detection system and a multiple skin lesion detection method that perform a process of situation-dependent decision determination so as to clearly distinguish and separately detect similar lesions existing on the skin of a user, and a computer-readable recording medium in which a program for implementing the same is recorded.

The present invention further provides a multiple skin lesion detection system and a multiple skin lesion detection method that can detect skin lesion objects having a relatively small size without loss, and a computer-readable recoding medium in which a program for implementing the same is recorded.

The present invention further provides a multiple skin lesion detection system and a multiple skin lesion detection method that may provide a user with a position of the detected skin lesion and a comprehensive skin lesion index, and recommend a customized product according to the comprehensive skin lesion index, and a computer-readable recording medium in which a program for implementing the same is recorded.

Technical Solution

The present invention has been devised to solve the above problems, therefore, the multiple skin lesion detection system of the present invention may include: an encoding unit that encodes user face image data and conducts feature extraction; a decoding unit located at the rear end of the encoding unit, which conducts mapping of the encoded user face image data to match an original image size and outputs a class value for each pixel; an operation unit that calculates a ratio of a detection class targeting a skin lesion ("a skin lesion-targeting detection class") occupied among the mapped classes relative to the entire face area so as to derive a skin lesion index; and an output unit that provides the user with an original image in which the skin lesion-targeting detection class is displayed, as well as the skin lesion index. The encoding unit may include: a regular convolution block that executes regular convolution operation on the user face image data; a residual block located at a rear end of the regular convolution block to conduct residual learning; and a rethinker block which is located at a rear end of the residual block and arranged alternately with the residual block, and extracts a local spatial correlation between multiple skin lesions within the user face image data so as to perform situation-dependent decision determination. Further, the decoding unit may include: an ASPP (Atrous Spatial Pyramid Pooling) module that executes atrous convolution operations at different extension ratios in parallel or an ASSPP (Atrous Separable Spatial Pyramid Pooling) module that executes atrous separable convolution operations in parallel.

In one embodiment, the encoding unit may conduct feature extraction of the user face image data using a deep-learning model that can separate and detect: $1^{st}$ to $11^{th}$ classes targeting different skin lesions; and a non-target class including the face and surrounding areas other than the $1^{st}$ to $11^{th}$ classes.

In one embodiment, the deep-learning model is characterized in that it is learned using a data set acquired by labeling the multiple face images into the $1^{st}$ to $11^{th}$ classes and the non-target class.

In one embodiment, the residual block may include at least one depthwise separable convolution layer that conducts depthwise separable convolution.

In one embodiment, the rethinker block may include: a convolutional LSTM layer to receive a feature map of the face image data that has passed through the residual block as an input value; and an SE block to conduct feature recalibration of the face image data that has passed through the convolutional LSTM layer.

In one embodiment, the rethinker block may include: a convolutional LSTM layer consisting of a first convolutional LSTM layer and a second convolutional LSTM layer; and an SE block to conduct feature recalibration of the face image data that has passed through the first convolutional LSTM layer, and may conduct a projection connection via the second convolutional LSTM layer.

In one embodiment, the SE block may include: a squeeze operation unit to extract important information on individual channels of the face image data that has passed through the convolutional LSTM layer; and an excitation operation unit to recalibrate the squeezed data so as to derive channel-wise dependencies.

In one example, the decoding unit may execute 1×1 convolution operation of 1×1 convolution operation result to a low-level feature map that passes through: a regular convolution block of the encoding unit; a residual block; or a rethinker block, and the user face image data that has passed through the ASPP (Atrous Spatial Pyramid Pooling) model or ASSPP (Atrous Separable Spatial Pyramid Pooling) module, followed by concatenating the up-sampled data.

In one embodiment, the output unit may recommend a customized product according to type of a skin lesion-targeting detection class and a skin lesion index.

The present invention also relates to a deep learning-based multiple skin lesion detection method using a deep learning-based multiple skin lesion detection system.

The multiple skin lesion detection method may include: encoding user face image data to conduct feature extraction; mapping the encoded user face image data to match an original image size and then outputting a class value for each pixel; deriving a skin lesion index by calculating a ratio of the skin lesion-targeting detection class occupied among the mapped classes relative to the entire face area; and providing the user with the original image in which the skin lesion-targeting detection class is displayed, as well as the skin lesion index.

In one embodiment, the process of conducting the feature extraction may include: executing a regular convolution operation on the user face image data; conducting residual learning on the user face image data on which the regular convolution operation has been executed; conducting a rethinking process of performing situation-dependent decision determination by extracting a local spatial correlation between multiple skin lesions in the user face image data on which the residual learning has been conducted.

In one embodiment, the process of outputting the class value for each pixel may include: executing atrous convolution operations at different extension ratios in parallel or executing atrous separable convolution operations in parallel; up-sampling stepwise the user face image data on which the atrous convolution or atrous separable convolution operations have been executed in parallel; and mapping the up-sampled user face image data to match an original image size and then outputting a class value for each pixel.

The present invention further relates to a computer-readable recording medium in which a program for implementing the deep learning-based multiple skin lesion detection method is recorded.

The present invention also relates to an electronic device to drive the recording medium.

In one embodiment, the electronic device may be, for example: a module for skin condition analysis in which the recording medium is stored; a kiosk including the above module; a mirror for skin condition diagnosis that includes the above module; a cosmetic vending machine that includes the above module and has skin condition diagnosis functions; a portable skin condition analysis device; or a portable terminal in which an application interworking with a server including the recording medium stored therein is installed.

Advantageous Effects

The deep learning-based multiple skin lesion detection system according to the present invention can clearly distinguish and separately detect similar skin lesions, and can detect lesions even having a small size without loss.

The deep learning-based multiple skin lesion detection system according to the present invention also provides the user with an image, in which the detected skin lesion is displayed, as well as a comprehensive skin lesion index, and recommends a customized product based on the type of the detected skin lesion and the comprehensive skin lesion index, whereby an accurate skin condition and an improvement method thereof can be provided to the user.

However, effects of the present invention are not limited by the above content.

DESCRIPTION OF DRAWINGS

FIG. is a block diagram showing a deep learning-based multiple skin lesion detection system according to the present invention.

DETAILED DESCRIPTION OF PREFERRED EMBODIMENTS OF INVENTION

Hereinafter, with regard to the present invention, a deep learning-based multiple skin lesion detection system, a deep learning-based multiple skin lesion detection method, a computer-readable recording medium in which a program for implementing the method is recorded, and an electronic device to drive the same will be described in more detail with reference to the accompanying drawings and embodiments thereof.

In the present specification, the singular expression includes the plural expression unless otherwise specified.

The terms used in this specification are selected among currently widely used general terms as possible while considering the functions in the present invention, however, may vary depending on the intention or precedent of those skilled in the art, the emergence of new technology, and the like. In addition, in a specific case, there is a term arbitrarily selected by the applicant and, at this time, the meaning of the above selected term will be described in detail in the description of the corresponding invention. Therefore, the terms used in the present invention should be defined based on the meanings of the terms and the content throughout the present invention, rather than the name of a simple term.

Embodiments of the present invention may be subjected to various transformations and may have various examples, and specific embodiments will be illustrated in the drawings and concretely stipulated in the detailed description. However, this is not intended to limit the scope of the specific embodiments, and it should be understood to include all modifications, equivalents and substitutes within the spirit and scope of the invention. In describing the embodiments, if it is determined that a detailed description of a related known technology may obscure the subject matter, the detailed description thereof will be omitted.

In the present specification, terms such as first, second, a and b may be used to describe various elements, but these elements should not be limited by the terms. The above terms are used only for the purpose of distinguishing one component from another.

In the present specification, terms such as "include(s)" or "comprise(s)" are intended to designate that the features, numbers, steps, operations, components, parts, or combinations thereof described in the specification are existing, but it is to be understood that the above terms do not preclude the possibility of addition or presence of one or more other features, numbers, steps, operations, components, parts, or combinations thereof.

In the present specification, terms such as "consists of" or "consisting of" are intended to designate that only the features, numbers, steps, operations, components, parts, or combinations thereof described in the specification are existing, and it should be understood that the above terms exclude the possibility of addition or presence of one or more other features, numbers, steps, operations, components, parts, or combinations thereof.

The present invention relates to a deep learning-based multiple skin lesion detection system.

Among various lesions present in the skin, it is common for one object to affect the existence and type of another object, but the current image processing technology and skin analysis device to which the above image processing technology is applied can only distinguish and detect a small number of skin lesions, however, there is a limitation in clearly distinguishing and detecting different skin lesions existing on the face of a user ("user face") by types of the lesions.

Accordingly, different kinds of lesions could be clearly distinguished and separately detected by applying a deep learning model designed on the basis of situation-dependent decision determination in consideration of a correlation between various types of skin lesions existing in the user face area and by designing an effective decoding structure to detect a small number of objects, therefore, the present inventor has developed a multiple skin lesion detection system that can detect all skin lesions without loss regardless of the size of objects.

More specifically, the deep learning-based multiple skin lesion detection system according to the present invention includes an encoding unit and a decoding unit, wherein the encoding unit is designed based on a modified aligned Xception skeleton and is configured to include a rethinker block that performs situation-dependent decision determination by extracting a local spatial correlation between multiple skin lesions, while the decoding unit is configured to include an ASPP (Atrous Spatial Pyramid Pooling) module or an ASSPP (Atrous Separable Spatial Pyramid Pooling) module, whereby problems of separable detection of various skin lesions and object loss in local skin lesions could be improved.

Figure 1:
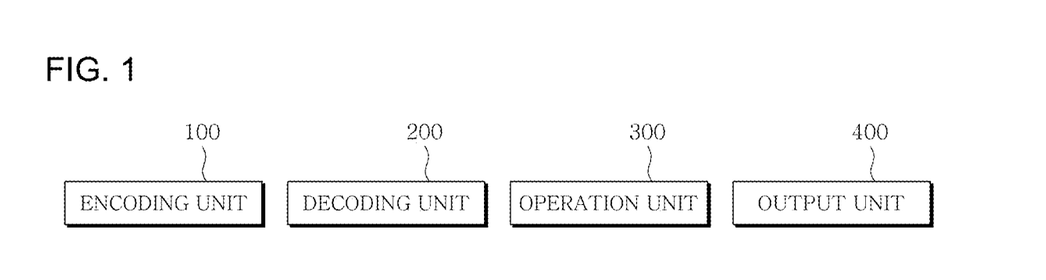
Figure 2:
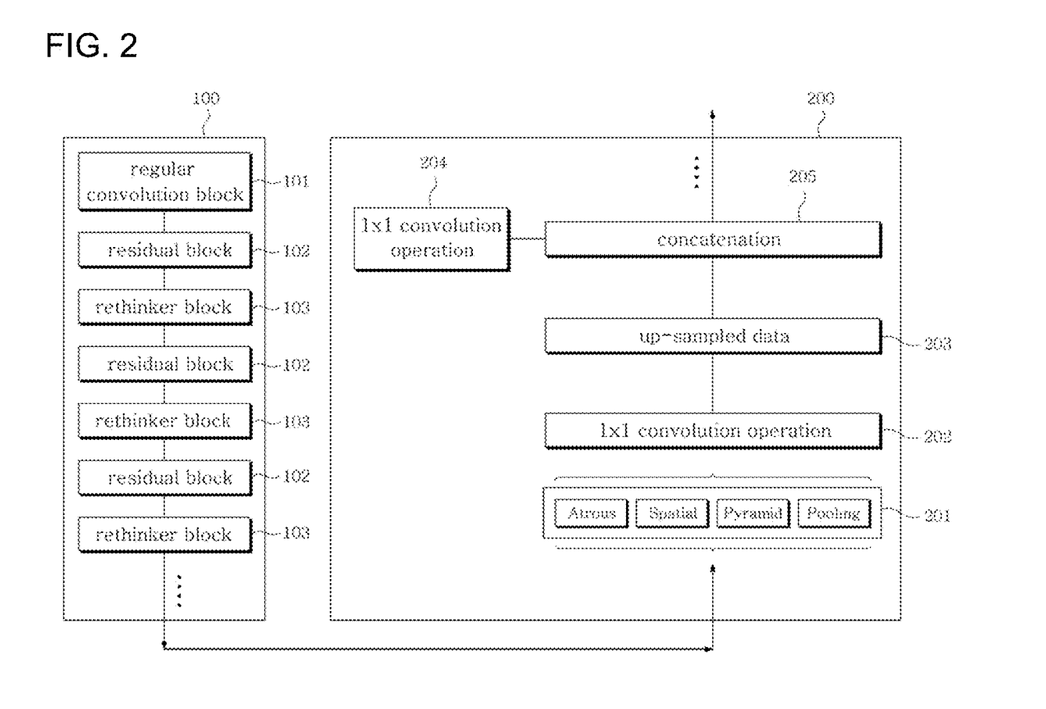
FIG. 2 illustrates a schematic block structure of an encoding unit and a decoding unit in the system according to the present invention.

FIG. 1 is a block diagram showing a deep learning-based multiple skin lesion detection system according to the present invention; and FIG. 2 illustrates a schematic block structure of the encoding unit 100 and the decoding unit 200 in the system according to the present invention.

As shown in FIG. 1, the multiple skin lesion detection system according to the present invention includes an encoding unit 100; a decoding unit 200; an (arithmetic) operation unit 300; and an output unit 400.

Further, as shown in FIG. 2, the encoding unit 100 may include a regular convolution block 101 that executes a regular convolution operation on data of the user face image; a residual block 102 located at the rear end of the regular convolution block 101 to conduct residual learning; and a rethinker block that is located at the rear end of the residual block and alternately arranged with the residual block 102, and extracts a local spatial correlation between multiple skin lesions in the user face image data so as to perform the situation-dependent decision determination.

Further, as shown in FIG. 2, the decoding unit 200 may include the ASPP (Atrous Spatial Pyramid Pooling) module 201 that executes atrous convolution operations at different extension ratios in parallel or the ASSPP (Atrous Separable Spatial Pyramid Pooling) module 201 that executes atrous separable operations in parallel.

The encoding unit 100 may encode the user face image data to conduct feature extraction.

Specifically, the encoding unit 100 forms a feature map for the obtained user face image data by resizing the photographed user face image and performs situation-dependent decision determination through a rethinker block, thereby serving to extract a local spatial correlation between multiple skin lesions in the user face image data.

More specifically, the encoding unit 100 may execute the regular convolution operation and residual learning of the user face image data using a deep-learning model that can separably detect: $1^{st}$ to $11^{th}$ classes targeting different skin lesions; and a non-target class including a face area and surrounding areas other than the $1^{st}$ to $11^{th}$ classes, followed by extracting a local spatial correlation between multiple skin lesions in the user face image data so as to perform context-dependent decision determination. Through an operation structure of the encoding unit 100 as described above, it is possible to accurately separate and detect various skin lesions without an error in distinguishing classes.

The regular convolution block 101 for executing a regular convolution operation using the deep-learning model may include at least one regular convolution layer, for example, may consist of 1 to 5, 1 to 4, 1 to 3, 2 or 1 regular convolution layer. When the regular convolution block 101 includes a plurality of regular convolution layers, parameters between the regular convolution layers may be the same or different depending on the type of the parameter.

The encoding unit 100 may include a residual block 102 located at the rear end of the regular convolution block 101 to conduct residual learning.

Figure 3:
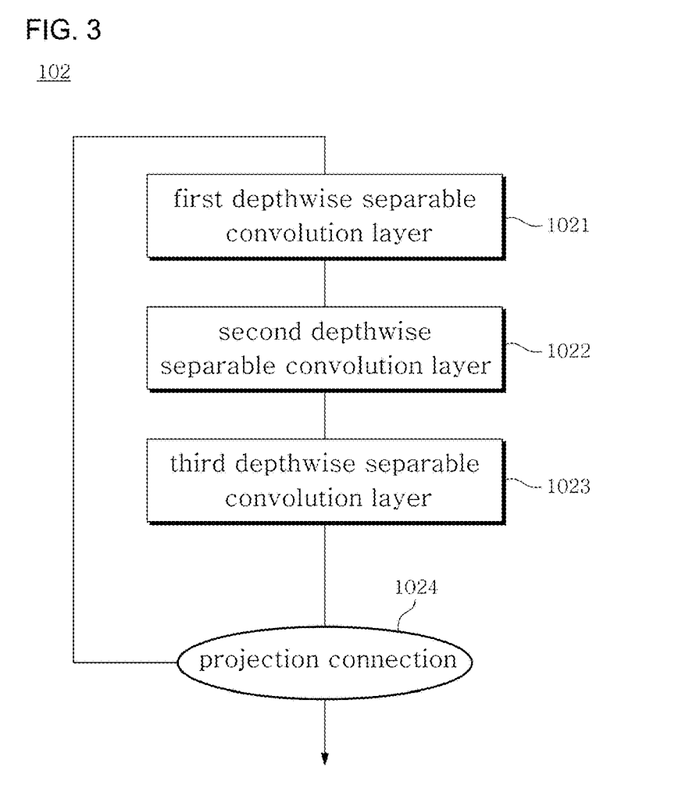
FIGS. 3 and 4 illustrate a structure of a residual block included in the encoding unit according to the present invention.
Figure 4:
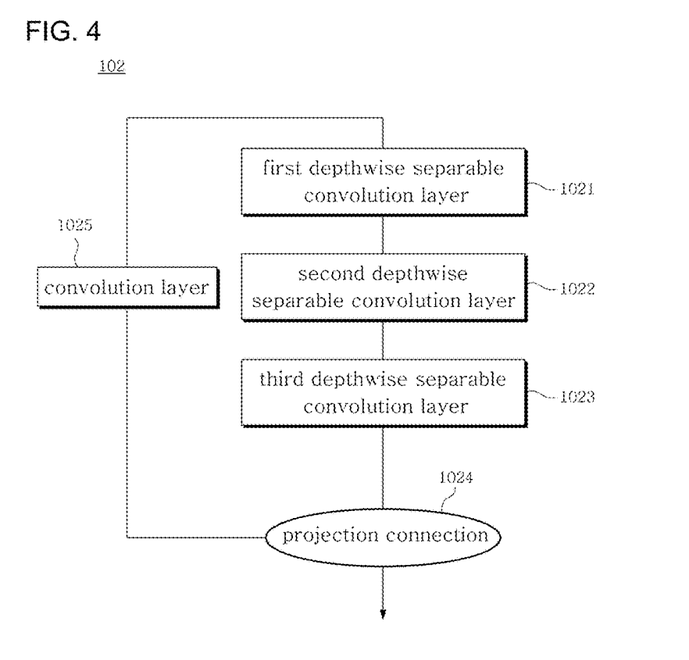

The residual block 102 means a block for conducting residual learning and may have, for example, the structure of FIG. 3 or FIG. 4. In the above description, the expression of "conducting residual learning" may mean conduct a skip connection represented by Equation 1 below or a projection connection represented by Equation 2 below.

$$H(x) = F(x) + x \quad \text{[Equation 1]}$$

$$H(x) = F(x) + Wx \quad \text{[Equation 2]}$$

In Equations 1 and 2, H(x) denotes a data value finally output through learning, F(x) denotes a residual operation value, x means an input value, W refers to linear projection for dimension matching.

In particular, the residual block 102 according to the present invention may be designed to allow the residual operation to be executed by a depthwise separable convolution layer that conducts depthwise separable convolution, thereby achieving effects of simplifying the parameters and minimizing the limitation of computing power.

In other words, the residual block 102 may include at least one depthwise separable convolution layer that conducts depthwise separable convolution.

Referring to the structure shown in FIG. 3, the residual block 102 may include first to third depthwise separable convolution layers 1021, 1022 and 1023 that conduct depthwise separable convolution.

Further, the residual block 102, as shown in FIG. 4, may include a convolution layer 1025 that conducts regular convolution for dimension matching, and the first to third depthwise separable convolution layers 1021, 1022 and 1023 that conduct depthwise separable convolution. Parameters of the first to third depthwise separable convolution layers 1021, 1022 and 1023 are each independently set, and may be the same or different from one another. The residual block 102 having the structure shown in FIG. 4 may conduct a projection connection 1024 for dimension matching.

The encoding unit 100 may also include the rethinker block 103 that is located at a rear end of the residual block 102, is alternately arranged with the residual block, and extracts a local spatial correlation between multiple skin lesions in the user face image data so as to perform situation-dependent decision determination.

The system of the present invention includes the rethinker block 103 to perform the situation-dependent decision determination by extracting a local spatial correlation between multiple skin lesions in the user face image data, thereby clearly separating and detecting different skin lesions.

Figure 5:
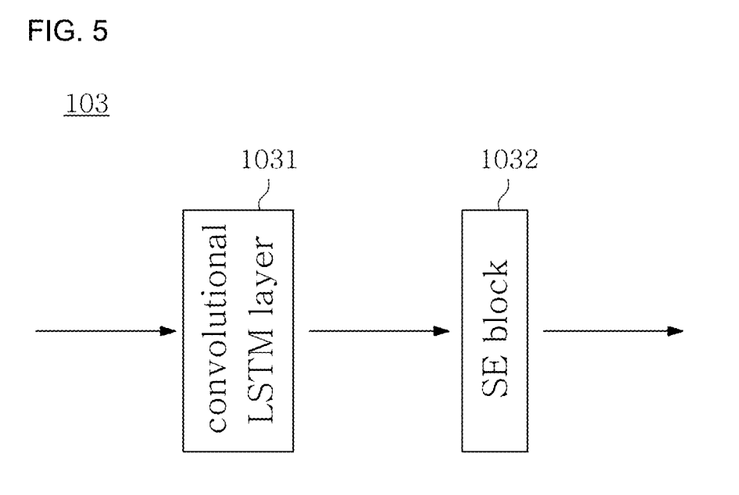
FIGS. 5 and 6 illustrate a structure of a rethinker block included in the encoding unit according to the present invention.
Figure 6:
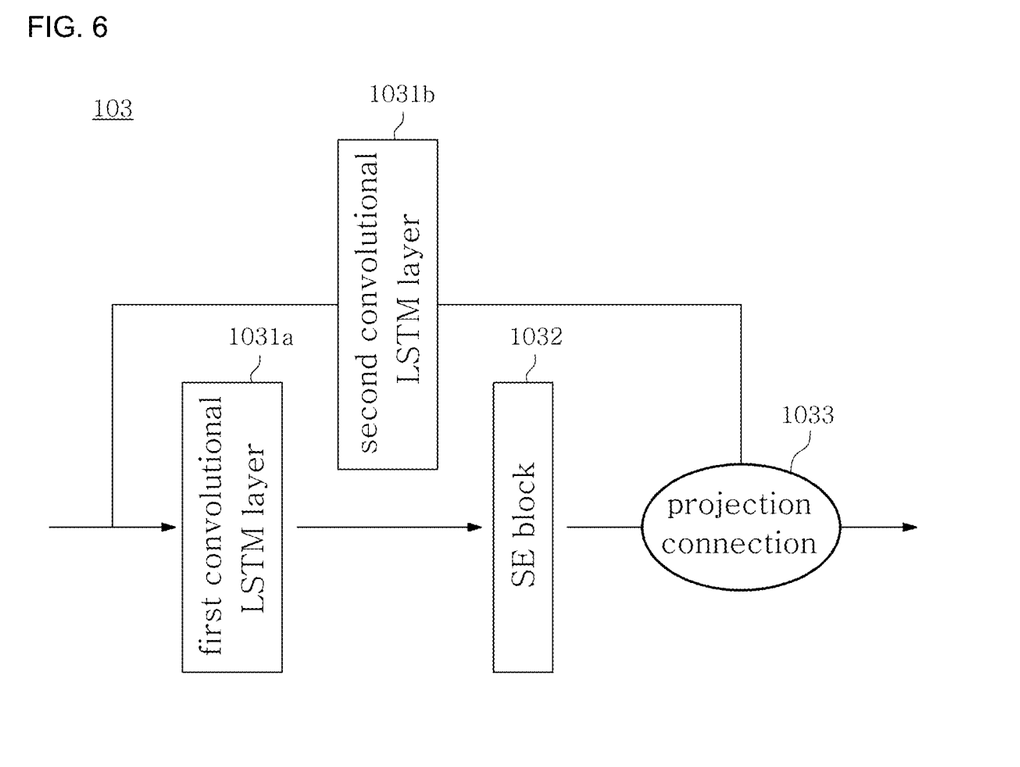

FIGS. 5 and 6 illustrate a structure of the rethinker block included in the encoding unit according to the present invention.

As shown in FIG. 5, the rethinker block 103 may include: a convolutional LSTM layer 1031 to receive a feature map of the face image data that has passed through the residual block 102; and an SE block 1032 to conduct feature recalibration of the face image data that has passed through the convolutional LSTM layer 1031.

The convolutional LSTM layer 1031, together with the SE block 1032, allows the encoding unit 100 to execute operation based on local spatial visibility dependency between features of objects to be detected ("detection objects") in the image while maintaining a wide spatial correlation.

The convolutional LSTM layer 1032 is particularly a locally designed convolutional LSTM layer and refers to an LSTM (Long Short-Term Memory) layer that executes Equations 3 to 7 below, has hidden-state and cell-state structures, and executes convolution operation.

$$i_t = \sigma(w_{vi} \odot v_t + W_{hi} \odot h_{t-1} + w_{ci} \circ c_{t-1} + b_i) \quad \text{[Equation 3]}$$

$$f_t = \sigma(w_{vf} \odot v_t + w_{hf} \odot h_{t-1} + w_{cf} \circ c_{t-1} + b_f) \quad \text{[Equation 4]}$$

$$c_t = f_t \circ c_{t-1} + i_t \circ \tanh(w_{xc} *_{v_t} + w_{hc} \odot h_{t-1} + b_c) \quad \text{[Equation 5]}$$

$$\sigma_t = \sigma(w_{vo} \odot v_t + w_{ho} \odot h_{t-1} + w_{co} \circ c_t + b_o) \quad \text{[Equation 6]}$$

$$h_t = o_t \circ \tanh(c_t) \quad \text{[Equation 7]}$$

In Equations 3 to 7, it is the input gate, $f_t$ is the forget gate, $c_t$ is the cell-state, Ht is the hidden-state, $\sigma_t$ is the output gate, $\odot$ means convolution operation, and $\circ$ means Hadamard product.

Figure 7:
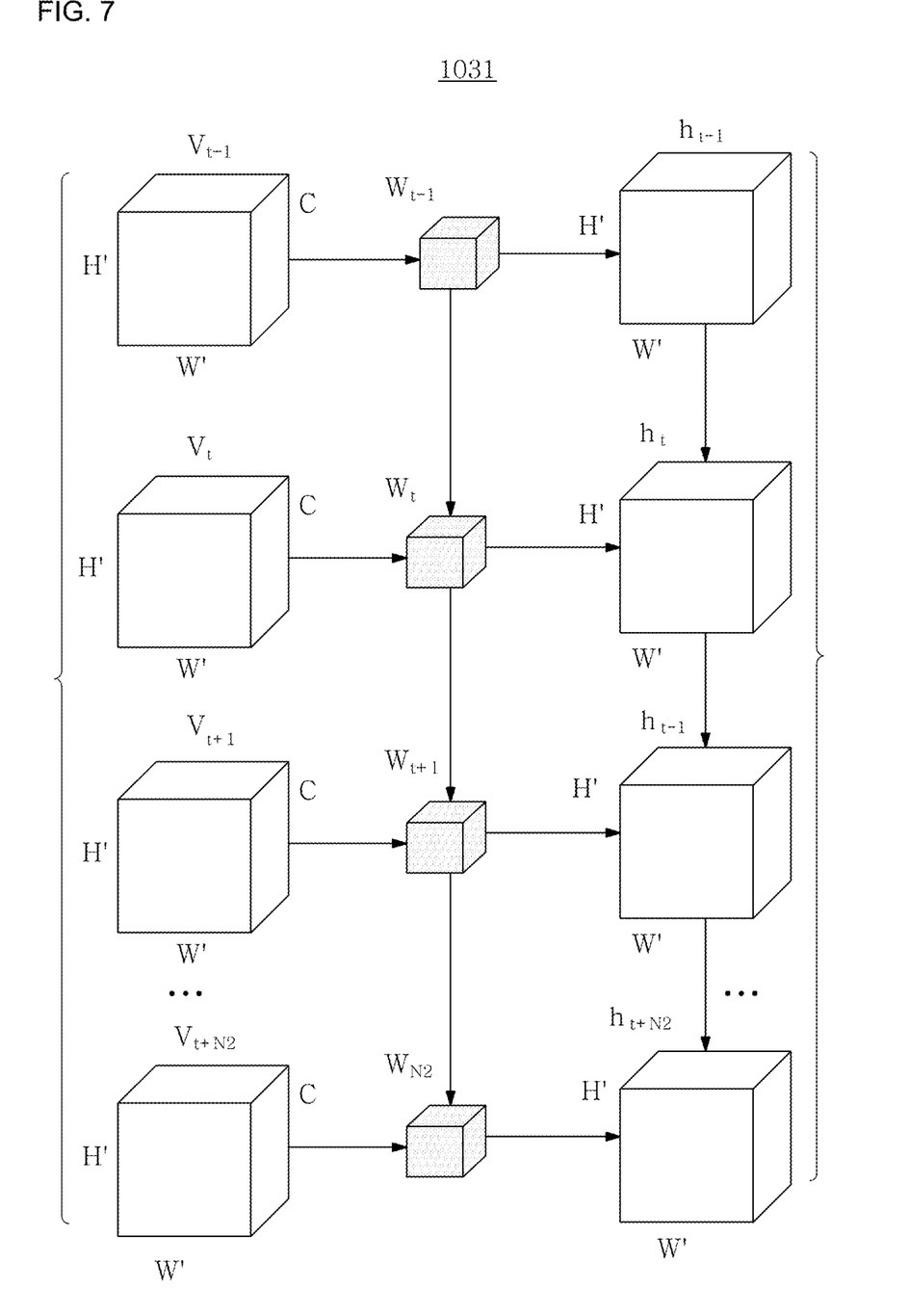
FIG. 7 illustrates an exemplary structure of a convolutional LSTM layer included in the rethinker block of the encoding unit according to the present invention.

The convolutional LSTM layer specifically has the structure illustrated in FIG. 7 and may receive, for example, dimension slicing data for a feature map channel of the face image data that has passed through the residual block 102 as an input value, and can provide an output value, that is, data having the same dimension as the feature map.

The rethinker block 103 may conduct a projection connection as shown in FIG. 6. In this case, the convolutional LSTM layer may consist of a first convolutional LSTM layer and a second convolutional LSTM layer.

In one embodiment, the rethinker block 103 may include: a convolutional LSTM layer 1031 consisting of a first convolutional LSTM layer 1031a and a second convolutional LSTM layer 1031b; and an SE block to conduct feature recalibration of the face image data that has passed through the first convolutional LSTM layer 1031a, and may conduct a projection connection 1033 via the second volutional LSTM layer 1031b as a medium. In this case, parameter values including the dimension slicing coefficients and kernel sizes of the first and second convolutional LSTM layers 1031a,b may be the same as or different from each other. The projection connection 1033 may be, for example, a sum operation or a multiplication operation and, preferably, a multiplication operation.

The rethinker block 103 may include an SE block 1032 to conduct feature recalibration of the face image data that has passed through the convolutional LSTM layer 1031.

The SE block 1032, together with the convolutional LSTM layer 1031, allows the encoding unit 100 to execute operation based on local spatial visibility dependency between features of the detection objects in the image while maintaining a wide spatial correlation.

The SE block 1032 means a block in which a squeeze operation and an excitation operation are executed, and may include a squeeze operation unit and an excitation operation unit.

The squeeze operation unit may have a role of extracting only important information for each individual channel by summarizing the entire information of the image data that has passed through the convolutional LSTM layer 1031. For example, GAP (Global average pooling) may be executed.

$$z_c = F_{sq}(v_c) \frac{1}{H \times W} \sum_{i=1}^{H} \sum_{j=1}^{W} v_c(i, j) \quad \text{[Equation 8]}$$

Equation 8 refers to a process of changing UV reflection image data of H, W and C sizes into 1, 1 and C sizes, summarizing the entire information of the data, and then extracting only important information for each channel.

The excitation operation unit may have a role of re-calibrating the squeezed image data and calculating channel-wise dependencies.

The excitation operation unit may consist of, for example, a fully connected layer and a non-linear function adjustment layer. The non-linear function adjustment layer may be, for example, a ReLU function layer or a sigmoid function layer, but is not limited thereto.

The SE block 1032 may further include a scaling unit that multiplies the data passed through the excitation operation unit and the input data before the squeeze operation unit. Through the scaling unit, data may be output at a scale before the squeeze operation unit.

Figure 8:
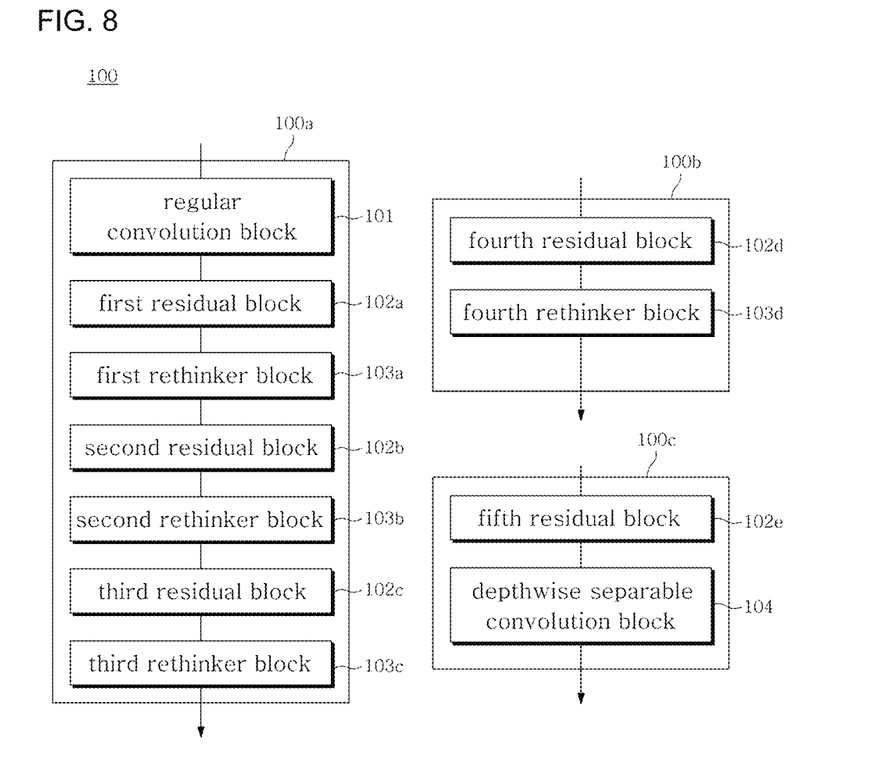
FIG. 8 concretely shows the detailed structure of the encoding unit according to the present invention.

FIG. 8 illustrates a detailed structure of the encoding unit 100 according to the present invention.

The encoding unit 100 may include an entry flow 100a, a middle flow 100b and an exit flow 100c including the aforementioned blocks.

The entry flow 100a may include a regular convolution block 101, a residual block 102, and a rethinker block 103 alternately arranged with the residual block 102.

More specifically, the entry flow 100a may consist of a regular convolution block 101, first to third residual blocks 102a, b and c, and first to third rethinker blocks 103a, b and c which are each placed between the first to third residual blocks 102a, b and c, respectively. The first to third residual blocks 102a, b and c of the entry flow 100a has the structure as shown in FIG. 4 and may conduct a projection connection.

The middle flow 100b may include a fourth residual block 102d and a fifth rethinker block 1003d.

More specifically, the middle flow 100b, the fourth residual block 102d and the fifth rethinker block 103d are alternately arranged by a plurality of times so as to repeat the operation executed in each block. The number of times for alternating arrangement may be, for example, 6 to 10 times, 7 to 9 times, or 8 times, but is not limited thereto. The fourth residual block 102d of the middle flow 100b has, for example, the structure as shown in FIG. 3, and may conduct skip connection.

The exit flow 100c may include a fifth residual block 102e and a depthwise separable convolution block 104 provided with at least one depthwise separable convolution layer that conducts depthwise separable convolution. The depthwise separable convolution lock 104 may include, for example, first to third depthwise separable convolution layers having the same or different parameters. Meanwhile, the fifth residual block 102e of the exit flow 100c has, for example, the structure as shown in FIG. 4, and may conduct a projection connection.

FIG. 8 is only one example of the detailed structure of the encoding unit 100 according to the present invention, but the above detailed structure does not limit other structural modification of the encoding unit 100.

As described above, the encoding unit 100 may conduct feature extraction of the user face image data using a deep-learning model that can separate and detect: $1^{st}$ to $11^{th}$ classes targeting different skin lesions; and a non-target class including the face and surrounding areas other than the above $1^{st}$ to $11^{th}$ classes.

In the above, the skin lesions targeted by the $1^{st}$ to $11^{th}$ classes may each independently include, for example, freckles, melasma, post-inflammatory pigmentation (PIH), age spots, whiteheads, papules, pustules, seborrheic dermatitis, flushing, redness and dots, but are not limited thereto.

The non-target class including the face and surrounding areas other than the $1^{st}$ to $11^{th}$ classes may include, for example, normal skin, hair, hair line, mouse, eyes, eyebrow, glasses, scarp/mask or background, etc., but is not limited thereto.

In one embodiment, the deep-learning model of the encoding unit 100 may be characterized in that it is learned using a data set obtained by labeling a plurality of face images into the $1^{st}$ to $11^{th}$ classes and the non-target class. In a more specific example, the deep-learning model may be characterized in that it is learned using a data set obtained by labeling a plurality of face images obtained from a population having at least one or more skin lesions as $1^{st}$ to $11^{th}$ classes indicating target skin lesions to be detected ("detection target lesions") and a non-target class indicating other areas.

Figure 9:
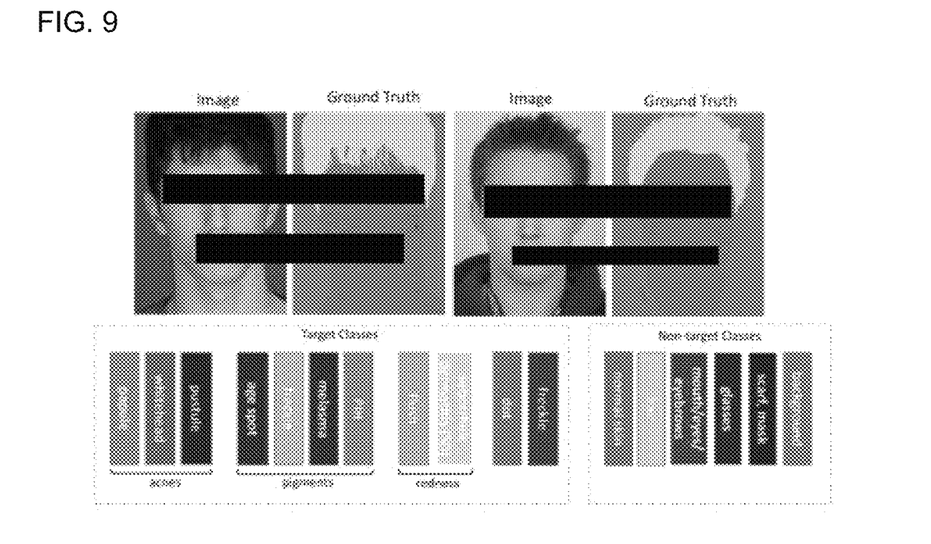
FIG. 9 illustrates an example of a data set obtained by labeling face images, which were introduced for designing a deep-learning model according to the present invention, by class.

FIG. 9 illustrates one example of a data set which was introduced for designing a deep-learning model according to the present invention.

As shown in FIG. 9, the data set introduced for model designing may include image data, which are labeled with preset classes, for example, classes indicating 11 skin lesions and a non-target class indicating other areas except for the above 11 skin lesions by a pixel-annotation-tool on a plurality of face images obtained from a population having at least one skin lesion. The image data may include a labeling color and a labeling name.

The decoding unit 200 is located at the rear end of the encoding unit and has a role of mapping the encoded user face image data to match the original image size and then outputting a class value for each pixel. The decoding unit 200 also includes an ASPP (Atrous Spatial Pyramid Pooling) module 201 that executes atrous convolution operations at different extension ratios in parallel or an ASSPP (Atrous Separable Spatial Pyramid Pooling) module 201 that executes atrous separable convolution operations in parallel.

Since the decoding unit has the above module structure, even a skin lesion of a small object can be detected without loss, and a problem caused by a limitation on computing power could be prevented in advance.

The ASPP (Atrous Spatial Pyramid Pooling) module 201 may execute atrous convolution operations at different extension ratios in parallel.

The atrous convolution operation refers to conducting convolution between an empty filter and input data at an extension ratio that denotes a specific interval. If the extension ratio exists as a parameter and when the extension ratio is increased, a wider area of image data can be contained.

The ASPP (Atrous Spatial Pyramid Pooling) module may execute atrous convolution operations at different extension ratios in parallel so as to decode information with different sizes without loss.

The ASSPP (Atrous Separable Spatial Pyramid Pooling) module may execute atrous separable convolution operation, specifically, a combined operation of atrous convolution and depthwise separable convolution. When using the ASSPP (Atrous Separable Spatial Pyramid Pooling) module 201, it is possible to maximize performance efficiency compared to parameter usage.

Figure 10:
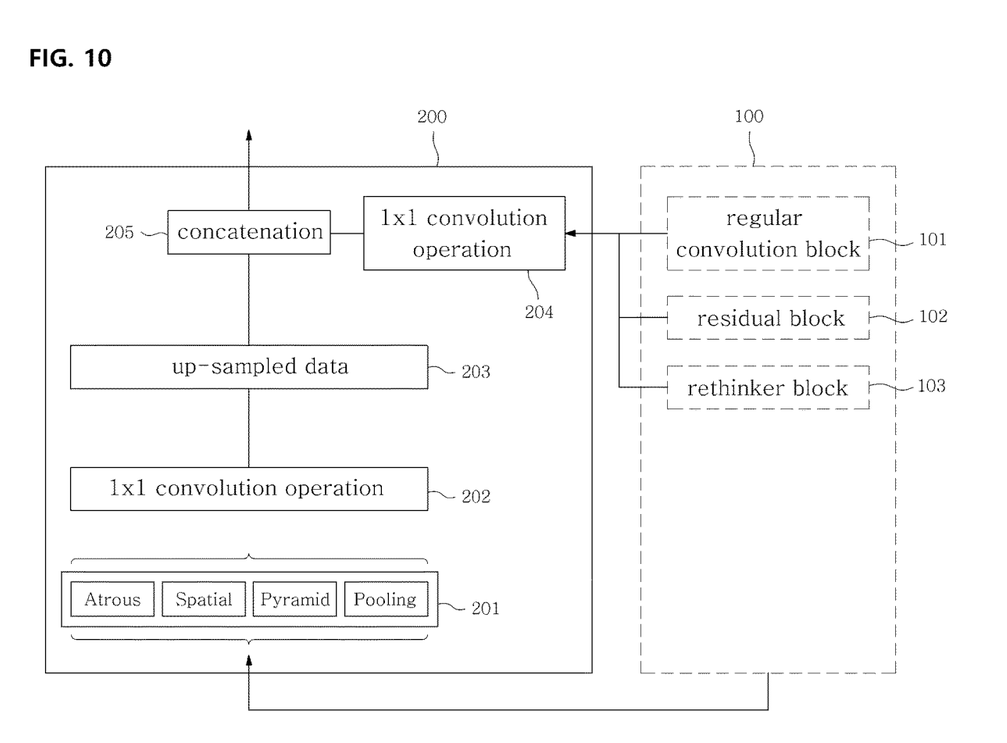
FIG. 10 concretely shows the detailed structure of the decoding unit according to the present invention.

FIG. 10 concretely illustrates a detailed structure of the decoding unit 200 according to the present invention.

As shown in FIG. 10, the decoding unit 200 may execute 1×1 convolution operation 202 of 1×1 convolution operation result 204 for a feature map passing the regular convolution block 101; the residual block 102; or the rethinker block 103 of the encoding unit 100 and the user face image data that have passed through the ASPP (Atrous Spatial Pyramid Pooling) module or the ASSPP (Atrous Separable Spatial Pyramid Pooling) module 201, followed by concatenation 205 of the up-sampled data 203.

The decoding unit 200 may have a structure to maximize the performance efficiency compared to the parameter usage, through the concatenation of a low-level feature map of the encoding unit 100 and the user face image data that have passed through the ASPP (Atrous Spatial Pyramid Pooling) module or the ASSPP (Atrous Separable Spatial Pyramid Pooling) module 201.

The structure shown in FIG. 10 is only an exemplary structure of the decoding unit 200 according to the present invention, and this structure does not limit the detailed structural modification of the decoding unit 200.

The decoding unit 200 may conduct mapping of the encoded user face image data to match the original image size and output a class value for each pixel through the aforementioned block configurations and structures.

The deep learning-based multiple skin lesion detection system of the present invention may further include an operation unit 300 that calculates a ratio of area occupied by the skin lesion-targeting detection class among the mapped classes, relative to the entire face area, followed by deriving a comprehensive skin lesion index.

Specifically, the operation unit 300 may derive the comprehensive skin lesion index by calculating a ratio of area occupied by the skin lesion-targeting detection class relative to the preset entire face area.

The comprehensive skin lesion index may be presented to the user as a numerical expression through the output unit 400 to be described below, but is not limited thereto. Alternatively, it may also be expressed as an arbitrary grade (A to D) or the like.

The deep learning-based multiple ski lesion detection system according to the present invention may include an output unit 400 that provides the user with an original image in which the skin lesion-targeting detection class is displayed, as well as the comprehensive skin lesion index.

The output unit 400 may provide an original image in which a skin lesion-targeting detection class is displayed, as well as a comprehensive skin lesion index, to the user on the basis of voice, display or communication signals. It should be understood that such provision of the original image, in which the skin lesion-targeting detection class is displayed, as well as the comprehensive skin lesion index, to the user by the output unit 400 may include: directly transmitting the voice or display signals from the output unit 400 to the user; but also introducing the display or communication signals to a separate device, and then, providing the user with the original image in which the skin lesion-targeting detection class is displayed, as well as the comprehensive skin lesion index through a voice or display means of the separate device.

The output unit 400 of the system according to the present invention may not only provide an original image, in which a skin lesion-targeting detection class is displayed, as well as a comprehensive skin lesion index, but also recommend customized products according to types of the skin lesion-targeting detection class and the comprehensive skin lesion index.

The system of the present invention may be implemented by a computer-readable recording medium, a module including the recording medium, or an electronic device in which the module is mounted.

The present invention also relates to a deep learning-based multiple skin lesion detection method using a deep learning-based multiple skin lesion detection system.

The skin lesion detection method may include: conducting feature extraction by encoding user face image data; mapping the encoded user face image data to match an original image size and then outputting a class value for each pixel; deriving a comprehensive skin lesion index by calculating a ratio of a skin lesion-targeting detection class occupied among the mapped classes, relative to the entire face area; and providing the original image, in which the skin lesion-targeting detection class is displayed, as well as the comprehensive skin lesion index, to the user.

According to the deep learning-based multiple skin lesion detection method of the present invention, it is possible to accurately separate and detect various skin lesions, and there is an advantage in that even small objects to be detected ("detection objects") can be detected without omission.

The process of conducting feature extraction by encoding user face image data may be executed by the encoding unit 100.

In one embodiment, the process of encoding the user face image data and conducting feature extraction may include: regular convolution operation executed by a regular convolution block; residual learning executed by a residual block; and rethinking for situation-dependent decision determination performed by a rethinker block of the encoding unit 100.

The process of mapping the encoded user face image data to match an original image size and then outputting a class value for each pixel may be executed by the decoding unit 200.

In one embodiment, the process of outputting a class value for each pixel may include: executing atrous convolution operations at different extension ratios in parallel or executing atrous separable convolution operations at different extension ratios in parallel; up-sampling stepwise the user face image data on which the atrous convolution or atrous separable convolution operations have been executed in parallel; and mapping the up-sampled user face image data to match an original image size and then outputting a class value for each pixel.

The process of deriving a comprehensive skin lesion index by calculating a ratio of a skin lesion-targeting detection class occupied among the mapped classes, relative to the entire face area; and the process of providing the original image, in which the skin lesion-targeting detection class is displayed, as well as the comprehensive skin lesion index, to the user may be conducted in the afore-mentioned operation unit 300 and the output unit 400, respectively, therefore, all of the above description in regard to the operation unit 300 and the output unit 400 would also be applied to the deep learning-based multiple skin lesion detection method according to the present invention.

Further, the present invention relates to a computer-readable recording medium in which a program for implementing a deep learning-based multiple skin lesion detection method is recorded.

Further, the present invention relates to an electronic device for executing the above recording medium. The electronic device may be, for example: a module for skin condition analysis in which the recording medium is stored; a kiosk including the above module; a mirror for skin condition diagnosis that includes the above module; a cosmetic vending machine that includes the above module and has skin condition diagnosis functions; a portable skin condition analysis device; or a portable terminal in which an application interworking with a server including the recording medium stored therein is installed.

In one embodiment, when the electronic device to execute the recording medium is a kiosk, the system of the present invention may be implemented in such a way that encoding, decoding and operation are executed in the skin condition analysis module, in which the recording medium is stored, on the basis of the user face image acquired through photographing functions of the kiosk; and the corresponding result is provided to the user through a display of the kiosk.

As described above, the deep learning-based multiple skin lesion detection system, the deep learning-based multiple skin lesion detection method, the computer-readable recording medium for implementing the above method, and the electronic device to execute the same according to the present invention have been described with reference to the accompanying drawings and embodiments. However, the above drawings and embodiments are only examples according to the present invention, and the scope of the present invention is not limited by the above description and various modifications and variations are possible from the contents described herein by those skilled in the art. Therefore, the scope of the present invention is not limited to the described embodiments but should be defined by the appended claims below, as well as equivalents thereof.

DESCRIPTION OF REFERENCE NUMERALS

100: Encoding unit
100a: Entry flow
100b: Middle flow
100c: Exit flow
101: Regular convolution block
102: Residual block
1021, 1022, 1023: First and second depthwise convolution layers
1024: Residual connection
1025: Convolution layer
102a, b, c, d, e: First to fifth residual blocks
103: Rethinking block
1031: Convolutional LSTM layer
1031a, b: First and second convolutional LSTM layers
1032: SE block
1033: Projection connection
103a, b, c, d: First to fourth rethinking blocks
104: Depthwise separable convolution
200: Decoding unit
201: ASPP module, ASSPP module
202, 204: 1×1 convolution operation
205: Concatenate
300: Operation unit
400: Output unit

The invention claimed is:

1. A deep learning-based multiple skin lesion detection system, comprising:
an encoding unit that encodes user face image data and conducts feature extraction;
a decoding unit located at the rear end of the encoding unit, which conducts mapping of the encoded user face image data to match an original image size and outputs a class value for each pixel;
an operation unit that calculates a ratio of a detection class targeting a skin lesion occupied among the mapped classes relative to the entire face area, so as to derive a comprehensive skin lesion index; and
an output unit that provides the user with an original image in which the skin lesion-targeting detection class is displayed, as well as the comprehensive skin lesion index,
wherein the encoding unit includes:
a regular convolution block that executes regular convolution operation on the user face image data;
a residual block located at a rear end of the regular convolution block to conduct residual learning; and
a rethinker block which is located at a rear end of the residual block and arranged alternately with the residual block, and extracts a local spatial correlation between multiple skin lesions within the user face image data, so as to perform situation-dependent decision determination,
wherein the decoding unit includes:
an ASPP (Atrous Spatial Pyramid Pooling) module that executes atrous convolution operations in parallel at different extension ratios or an ASSPP (Atrous Separable Spatial Pyramid Pooling) module that executes atrous separable convolution operations in parallel.

2. The system according to claim 1, wherein the encoding unit conducts feature extraction of the user face image data using a deep-learning model, and
wherein the deep-learning model is characterized in that it is learned using a data set acquired by labeling multiple face images into the $1^{st}$ to $11^{th}$ classes and the non-target class.

3. The system according to claim 1, wherein the residual block includes
at least one depthwise separable convolution layer that conducts depthwise separable convolution.

4. The system according to claim 1, wherein the rethinker block includes:
a convolutional LSTM layer to receive a feature map of the face image data that has passed through the residual block as an input value; and
an SE block to conduct feature recalibration of the face image data that has passed through the convolutional LSTM layer.

5. The system according to claim 1, wherein the rethinker block includes:
a convolutional LSTM layer consisting of a first convolutional LSTM layer and a second convolutional LSTM layer; and
an SE block to conduct feature recalibration of the face image data that has passed through the first convolutional LSTM layer, and
wherein the rethinker block conducts a projection connection via the second convolutional LSTM layer.

6. The system according to claim 4, wherein the SE block includes:
a squeeze operation unit to extract important information on individual channels of the face image data that has passed through the convolutional LSTM layer; and
an excitation operation unit to recalibrate the squeezed data so as to derive channel-wise dependencies.

7. The system according to claim 1, wherein the decoding unit is configured to:
execute 1×1 convolution operation on the user face image data that has passed through the ASPP (Atrous Spatial Pyramid Pooling) model or ASSPP (Atrous Separable Spatial Pyramid Pooling) module,
up-sample the user face image data on which 1×1 convolution operation has been executed, and
concatenate the up-sampled user face image data and the 1×1 convolution operation result of a feature map that passes through: a regular convolution block of the encoding unit; a residual block; or a rethinker block.

8. The system according to claim 1, wherein the output unit recommends a customized product according to type of the skin lesion-targeting detection class and the comprehensive skin lesion index.

9. A deep learning-based multiple skin lesion detection method performed using the deep learning-based multiple skin lesion system according to claim 1, the method comprising:
- encoding user face image data to conduct feature extraction;
- mapping the encoded user face image data to match an original image size and then outputting a class value for each pixel;
- deriving a comprehensive skin lesion index by calculating a ratio of the skin lesion-targeting detection class occupied among the mapped classes relative to the entire face area; and
- providing the user with the original image in which the skin lesion-targeting detection class is displayed, as well as the comprehensive skin lesion index.

10. The method according to claim 9, wherein the process of conducting the feature extraction includes:
- executing a regular convolution operation on the user face image data;
- conducting residual learning on the user face image data on which the regular convolution operation has been executed;
- conducting a rethinking process of performing situation-dependent decision determination by extracting a local spatial correlation between multiple skin lesions in the user face image data on which the residual learning has been conducted.

11. The method according to claim 9, wherein the process of outputting the class value for each pixel includes:
- executing atrous convolution operations at different extension ratios in parallel or atrous separable convolution operations in parallel;
- up-sampling stepwise the user face image data on which the atrous convolution or atrous separable convolution operations have been executed in parallel; and
- mapping the up-sampled user face image data to match an original image size and then outputting a class value for each pixel.

12. A non-transitory computer-readable recording medium in which a program for implementing the deep learning-based multiple skin lesion detection method according to claim 9 is recorded.

13. An electronic device to drive the recording medium according to claim 12.

14. The electronic device according to claim 13, wherein the electronic device is:
- a module for skin condition analysis in which the recording medium is stored; a kiosk including the above module; a mirror for skin condition diagnosis that includes the above module; a cosmetic vending machine that includes the above module and has skin condition diagnosis functions; a portable skin condition analysis device; or a portable terminal in which an application interworking with a server including the recording medium stored therein is installed.

* * * * *